US00PP13647P29

(12) United States Plant Patent
Plevier

(10) Patent No.: US PP13,647 P2
(45) Date of Patent: Mar. 11, 2003

(54) ALSTROEMERIA PLANT NAMED 'OSSORIO'

(76) Inventor: Franciscus Bernardus Plevier, Hoofdstraat 56a, 2171 AV Sassenheim (NL)

( * ) Notice: Subject to any disclaimer, the term of this patent is extended or adjusted under 35 U.S.C. 154(b) by 0 days.

(21) Appl. No.: 10/080,594

(22) Filed: Feb. 22, 2002

(51) Int. Cl.[7] ..... A01H 5/00

(52) U.S. Cl. ..... Plt./309

(58) Field of Search ..... Plt./309

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Alstroemeria plant named 'Ossorio', characterized by its erect flowering stems; yellow flowers with red apices and dark purple spots; and excellent postproduction longevity.

1 Drawing Sheet

BOTANICAL CLASSIFICATION/CULTIVAR DESIGNATION

*Alstroemeria hybrida* cultivar Ossorio.

BACKGROUND OF THE INVENTION

The present Invention relates to a new and distinct cultivar of Alstroemeria plant, botanically known as *Alstroemeria hybrida*, commercially used as a cut flower Alstroemeria, and hereinafter referred to by the name 'Ossori'.

The new Alstroemeria is a product of a planned breeding program conducted by the Inventor in Hillegom, The Netherlands. The objective of the breeding program was to develop new cut flower Alstroemeria cultivars with attractive flower colors and excellent postproduction longevity.

The new Alstroemeria originated from a cross made by the Inventor in Hillegom, The Netherlands of two unidentified selections of *Alstroemeria hybrida*, not patented. The new Alstroemeria was discovered and selected by the Inventor as a flowering plant within the progeny of the stated cross in a controlled environment in Hillegom, The Netherlands in 1994. The selection of this new Alstroemeria was based on its attractive flower colors.

Asexual reproduction of the new cultivar by root divisions taken in a controlled environment in Rijsenhout, The Netherlands, has shown that the unique features of this new Alstroemeria are stable and reproduced true to type in successive generations of asexual propagation.

SUMMARY OF THE INVENTION

Plants of the cultivar Ossorio have not been observed under all possible environmental conditions. The phenotype may vary somewhat with variations in environment such as temperature and light intensity without, however, any variance in genotype.

The following traits have been repeatedly observed and are determined to be the unique characteristics of 'Ossorio'. These characteristics in combination distinguish 'Ossorio' as a new and distinct cultivar:

1. Erect flowering stems.
2. Yellow flowers with red apices and dark purple spots.
3. Excellent postproduction longevity.

Plants of the new Alstroemeria are most similar to plants of the parent selections, however plants of the new Alstroemeria differ from plants of the parent selections primarily in flower coloration.

BRIEF DESCRIPTION OF THE PHOTOGRAPH

The accompanying colored photograph illustrates the overall appearance of the new Alstroemeria, showing the colors as true as it is reasonably possible to obtain in colored reproductions of this type. Colors in the photograph may differ slightly from the color values cited in the detailed botanical description which accurately describe the colors of the new Alstroemeria. The photograph comprises a side perspective view of a typical flowering stem of 'Ossorio'.

DETAILED BOTANICAL DESCRIPTION

The aforementioned photographs, following observations, measurements and values describe plants of the new Alstroemeria grown in Rijsenhout, The Netherlands in a glass-covered greenhouse in ground beds. During the production of the plants, day temperatures ranged from 10 to 15° C. and night temperatures ranged from 5 to 10° C. Plants used for the photograph and description were about 12 months from planting root divisions.

Color references are made to The Royal Horticultural Society Colour Chart, 1995 Edition, except where general terms of ordinary dictionary significance are used.

Botanical classification: *Alstroemeria hybrida* cultivar Ossorio.

Parentage:

*Female parent.*—Unidentified selection of *Alstroemeria hybrida*, not patented.

*Male parent.*—Unidentified selection of *Aistroemeria hybrida*, not patented.

Propagation:

*Type.*—By root divisions.

*Root description.*—Fibrous; white, 155A, in color.

*Rooting habit.*—Freely branching.

*Rhizomes.*—Shape: Round. Diameter: About 10 to 30 cm. Texture: Smooth. Color: 155D.

Plant description:

*Plant habit.*—Upright; freely basal branching, bushy appearance. Time from planting to harvest of cut flowers: About 90 to 100 days.

*Number of flowering stems produced per year.*—About 180 to 200.

*Plant height.*—About 140 to 180 cm.

*Plant diameter* (*spread*).—At base of plant: About 25 to 35 cm. At top of plant: About 50 to 80 cm.

*Flowering stem description.*—Aspect: Erect. Length: About 110 to 160 cm. Diameter: About 8 to 10 mm. Internode length: About 10 cm. Strength: Strong. Texture: Smooth, glabrous. Color: 144A.

*Foliage description.*—Leaves asymmetrical; sessile. Length: About 4 to 18.5 cm. Width: About 1 to 3 cm. Shape: Elliptical. Apex: Acute. Base: Attenuate. Margin: Entire, minutely crimped. Texture: Upper surface: Smooth, glabrous. Lower surface: Rough, glabrous. Venation pattern: Parallel. Color: Young and fully developed foliage, upper surface: 137B. Young and fully developed foliage, lower surface: 137C. Venation, upper surface: Close to 137B. Venation, lower surface: Close to 137C.

Flower description:

*Flower type and habit.*—Single cup-shaped flowers arranged in compound umbels. Perianth segments separate. Freely and continuously flowering. Flowers persistent.

*Natural flowering season.*—Flowering continuous from the spring through the fall in The Netherlands.

*Fragrance.*—None detected.

*Flower longevity on the plant.*—About four weeks.

*Flower longevity as a cut flower.*—About 20 to 25 days.

*Flower buds* (*showing color*).—Length: About 2 to 4 cm. Diameter: About 1 to 2 cm. Shape: Ovoid. Color: 155A.

*Umbel length.*—About 13 to 16 cm.

*Umbel diameter.*—About 19 to 26 cm.

*Number of flowers per umbel.*—About 12 to 20.

*Flower diameter.*—About 6.5 cm.

*Flower depth* (*height*).—About 6 cm.

*Perianth.*—Arrangement: Six arranged in two whorls. Size: Inner perianth segment: Length: About 5.2 cm. Width: About 2.9cm. Outer perianth segment: Length: About 5.7 cm. Width: About 3.1 cm. Shape: Inner perianth segments: Lanceolate. Outer perianth segments: Obovate. Apex: Inner perianth segment: Acute to cuspidate. Outer perianth segments: Cuspidate with emarginate tendencies. Base: Attenuate. Margin: Entire, minutely crimped. Texture: Smooth, glabrous; velvety. Color: Inner perianth segments: When opening and fully opened, upper surface: 2C; towards the apex, 47A, at apex, close to 144A; towards the base, 4A. Lateral segments with 30 to 50 spots, 187A; lower segment with 5 to 15 spots, 187B. When opening and fully opened, lower surface: 4A. Outer perianth segments: When opening and fully opened, upper surface: 2C; towards the base, 2D; central longitudinal stripe, close to 144A. When opening and fully opened, lower surface: 2D.

*Pedicels.*—Length: About 1 to 4 cm. Diameter: About 3 mm. Strength: Strong. Aspect: Erect. Texture: Smooth, glabrous. Color: 144A.

*Reproductive organs.*—Stamens: Quantity per flower: Six. Anther length: About 5 to 10 mm. Anther color: 152C. Filament length: About 3 to 4 mm. Filament color: 28D. Pollen color: 152B. Pistils: Quantity per flower: One. Stigma color: 28C. Style length: About 4 to 5 cm. Style color: 28D.

*Fruit.*—Shape: Ovoid. Color: 163A. Fertile: No.

Disease/pest resistance: Plants of the new Alstroemeria has not been observed to be resistant to pathogens and pests common to Alstroemerias.

It is claimed:

1. A new and distinct cultivar of Alstroemeria plant named 'Ossorio', as illustrated and described.

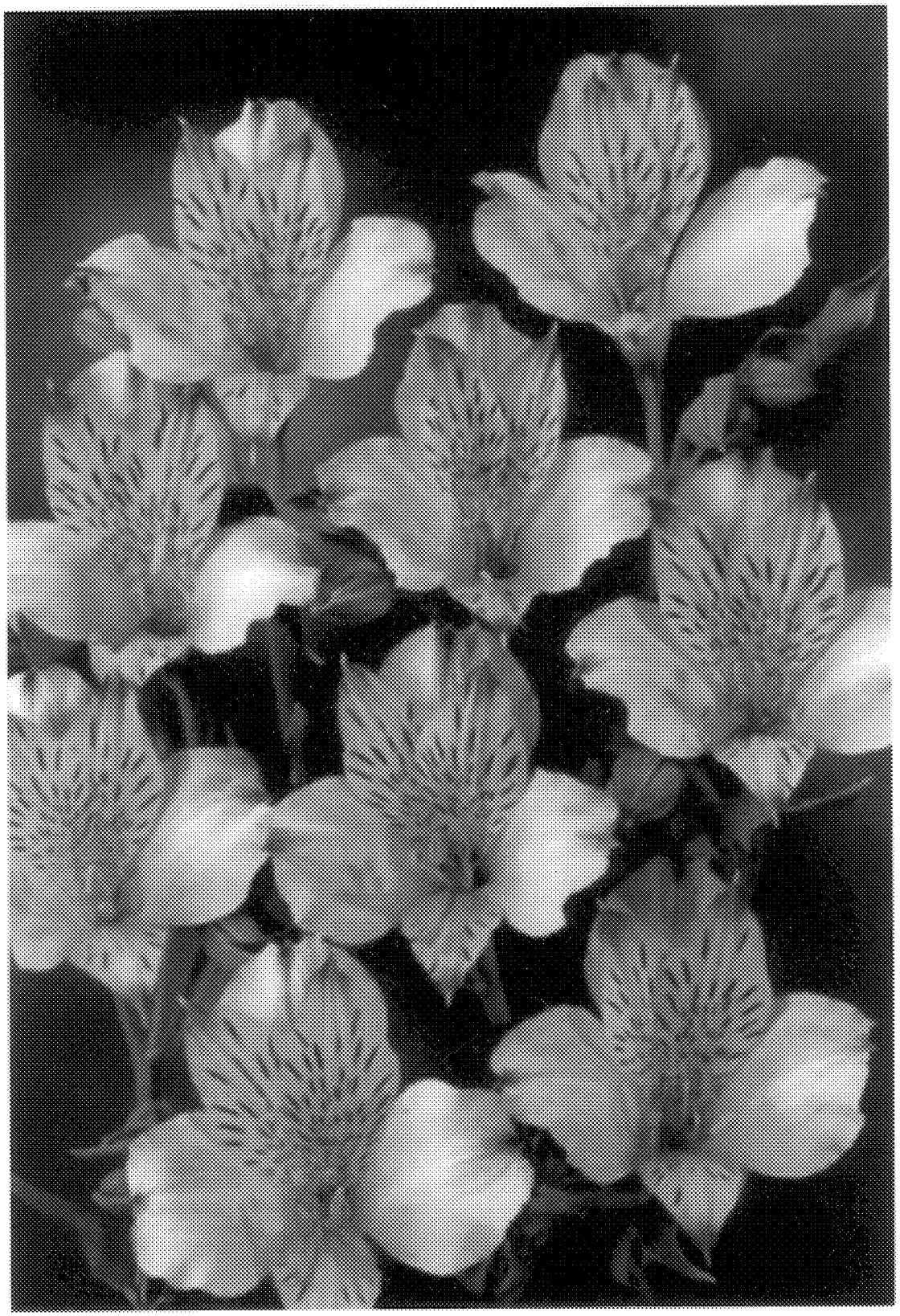

* * * * *